US006486150B2

(12) United States Patent
Hunke et al.

(10) Patent No.: US 6,486,150 B2
(45) Date of Patent: Nov. 26, 2002

(54) PROCESS FOR FORMULATION OF ANTIBIOTIC COMPOUNDS

(75) Inventors: William A. Hunke, Harleysville, PA (US); Kathleen J. Illig, Phoenixville, PA (US); Anand Kanike, Lansdale, PA (US); Scott D. Reynolds, Perkiomenville, PA (US); Stelios C. Tsinontides, Ambler, PA (US); Anthony S. Al-Dehneh, Voorhees, NJ (US); Hiren S. Patel, Parsippany, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/845,453

(22) Filed: Apr. 27, 2001

(65) Prior Publication Data

US 2002/0002160 A1 Jan. 3, 2002

Related U.S. Application Data

(63) Continuation-in-part of application No. 09/698,808, filed on Oct. 27, 2000.
(60) Provisional application No. 60/162,482, filed on Oct. 29, 1999.
(51) Int. Cl.$^7$ .............................................. A61K 31/407
(52) U.S. Cl. .................. 514/210.13; 540/350
(58) Field of Search ...................... 514/210.13; 540/350

(56) References Cited

U.S. PATENT DOCUMENTS 5,478,820 A     12/1995  Betts et al.
5,652,233 A      7/1997  Betts et al.
5,952,323 A  *   9/1999  Zimmerman et al. .. 514/210.13
6,180,783 B1 *   1/2001  Williams et al. ............ 540/350
6,297,231 B1 * 10/2001  Almarsson et al. .... 514/210.13

FOREIGN PATENT DOCUMENTS

WO      WO 93/15078        8/1993

OTHER PUBLICATIONS

Betts et al., Chem. Abs. 118: 80721, 1992.
Peter A. S. Smith, The Chemistry of Open–Chain Organic Nitrogen Compounds, vol. 1, p. 263, 1965.

* cited by examiner

Primary Examiner—Mukund J. Shah
Assistant Examiner—Thomas C. McKenzie
(74) Attorney, Agent, or Firm—Sylvia A. Ayler; Mark R. Daniel

(57) ABSTRACT

The present invention involves a process for preparing a stable final formulation product of a compound of formula I,

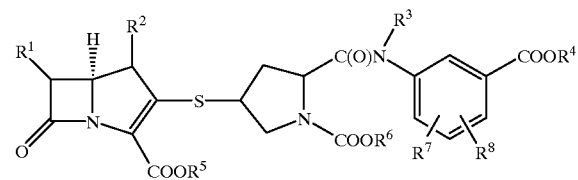

or its pharmaceutically acceptable salt, hydrate or solvate by incorporating a suitable carbon dioxide source to an unstable monosodium adduct of carbapenem antibiotic compound.

40 Claims, No Drawings

PROCESS FOR FORMULATION OF ANTIBIOTIC COMPOUNDS

CROSS-REFERENCE TO RELATED APPLICATIONS

This application is a continuation-in-part (CIP) application of U.S. Ser. No. 09/698,808, filed Oct. 27, 2000, which claims the benefit of Provisional application Ser. No. 60/162,482, filed Oct. 29, 1999.

FIELD OF THE INVENTION

The present invention relates to a process for preparing a stabilized form of antibiotic compounds, in particular a carbapenem antibiotic composition.

BACKGROUND OF THE INVENTION

Betalactams, a broader class of antibiotics which is further defined as carbapenems are useful for the treatment of infectious diseases including gram positive and negative, and aerobic and anaerobic bacteria. Carbapenems were first isolated from fermentation media in 1974 and were found to have broad-spectrum antibacterial activity. Since this discovery substantial investigations have been made into new carbapenem derivatives and many hundreds of patents and scientific papers have been published. The commercially marketed carbapenem is imipenem (N-formimidoyl thienamycin), which has a broad range of antibacterial activity. This compound can be used in the treatment of any disease that is conventionally treated with antibiotics, for example in the treatment of bacterial infection in mammals including humans.

It has been reported that dimerization of carbapenem is inhibited via the formation of a reversible equilibrium adduct between carbon dioxide and monosodium salt of carbapenem compound as shown below, where $K_a$ and $K_{eq}$ are equilibrium constants of the reactions.

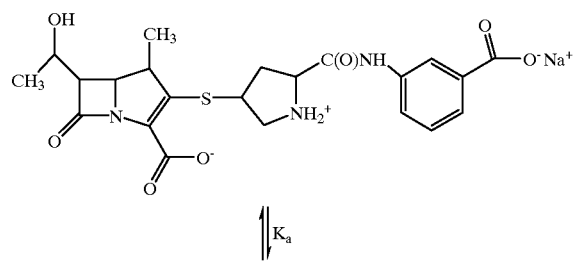

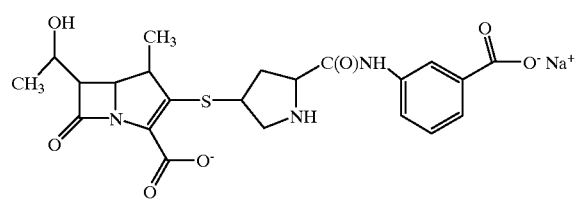

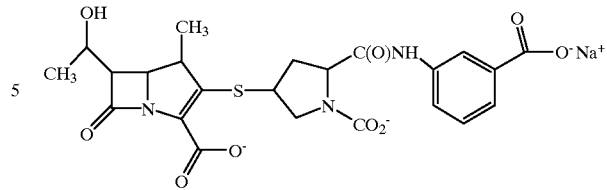

During the manufacture of bulk antibiotic products such as carbapenem antibiotic, the pharmaceutical compound is prepared by chemical synthesis from raw materials in large quantities. Carbapenem antibiotic compounds are prepared in large batches as salt form, monosodium salt as shown above, which are weak crystalline solids, hygroscopic at ambient conditions, and unstable at room and refrigerated temperatures. Because the compound is unstable at a temperature above about $-20°$ C., the bulk compounds must be stored at a low temperature (about $-20°$ C.) to prevent degradation into dimers or open ring by-products. Although the unstable compound of carbapenem, after bulk manufacturing, can be stored for long periods of time at a low temperature, it must be converted into a stable formulation prior to use as once-a-day antimicrobial agent for intravenous (IV) or intramuscular (IM) administration.

Several reported cases for preparing carbapenem antibiotic compounds have shortcomings of teaching how to achieve a stable form of carbapenem antibiotics in its final formulation and manufacturing process. In particular, they fail to teach how to achieve the conversion of salt-containing carbapenem compound to a formulation exhibiting acceptable levels of degradates required for solid state and reconstitution stability for dosing to patients.

For example, Almarsson et al. (WO 98/18800) discloses a method for stabilizing carbapenem antibiotics by carboxylating the pyrrolidinyl amino acid with a carbon dioxide source, but fails to teach the steps necessary to obtain the stable form of carbapenem during its formulation process.

Zimmerman et al. (U.S. Pat. No. 5,952,323) relates a method of stabilizing a carbapenem compound by incorporating carbon dioxide source, but it also does not provide how to achieve the stabilized form of carbon dioxide adduct in its final composition.

In light of the above, an objective of the present invention is to provide a process for formulating a final product of stable antibiotic compound, in particular carbapenem antibiotic for the treatment of infectious diseases which include gram positive and negative, and aerobic and anaerobic bacteria. Another object of the present invention is to provide a novel manufacturing process to prepare the final formulation product of carbapenem antibiotic with acceptable levels of degradates, solid state stability and solution stability for dosing.

SUMMARY OF THE INVENTION

The present invention is directed to a process for preparing a final formulation product of a compound of Formula I,

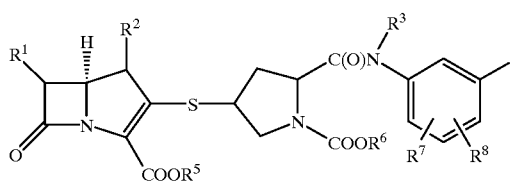

or its pharmaceutically acceptable salt, hydrate or solvate wherein, $R^1$ is:
(a) 1-hydroxyethyl,
(b) 1-fluoroethyl, or
(c) hydroxymethyl;

$R^2$ and $R^3$ are independently:
(a) hydrogen, or
(b) $(C_1-C_6)$-alkyl;

$R^4$, $R^5$ and $R^6$ are independently
(a) hydrogen
(b) $(C_1-C_6)$-alkyl, or
(c) alkali-metal or alkali earth-metal wherein the alkali-metal or alkali earth-metal is sodium, potassium, lithium, cesium, rubidium, barium, calcium or magnesium; and $R^7$ and $R^8$ are independently:
(a) hydrogen,
(b) halo,
(c) cyano,
(d) $(C_1-C_6)$-alkyl,
(e) nitro,
(f) hydroxy,
(g) carboxy,
(h) $(C_1-C_6)$-alkoxy,
(i) $(C_1-C_6)$-alkoxycarbonyl,
(j) aminosulphonyl,
(k) $(C_1-C_6)$-alkylaminosulphonyl,
(l) di-$(C_1-C_6)$-alkylaminosulphonyl,
(m) carbamoyl,
(n) $(C_1-C_6)$-alkylcarbamoyl,
(o) di-$(C_1-C_6)$-alkylcarbamoyl,
(p) trifluoromethyl,
(q) sulphonic acid,
(r) amino,
(s) $(C_1-C_6)$-alkylamino,
(t) di-$(C_1-C_6)$-alkylmino,
(u) $(C_1-C_6)$-alkanoylamino,
(v) $(C_1-C_6)$-alkanoyl(N-$(C_1-C_6)$-alkyl)amino,
(w) $(C_1-C_6)$-alkanesulphonamido, or
(x) $(C_1-C_6)$-alkyl-$S(O)_n$ wherein n is 0–2;

comprising the steps of:
(1) charging a solution of carbon dioxide source having a pH range of about 6.0 to about 12.0 into a reaction vessel;
(2) adding an effective amount of a mole ratio of a base and an active ingredient into the reaction vessel containing the solution of carbon dioxide source to maintain pH at about 6.0 to about 9.0 and a temperature range of about -3° C. to about 15° C.;
(3) lyophilizing the solution of Step (2) to yield the final formulation product of a compound of formula I with less than about 10% of moisture content.

DETAILED DESCRIPTION OF THE INVENTION

The present invention relates to a process for preparing a stable form of carbapenem compound in its formulation and manufacturing processes. More specifically, the present invention involves a process for preparing a stabilized carbon dioxide adduct of carbapenem antibiotic by incorporating suitable carbon dioxide source to unstable salt form of carbapenem antibiotic, in particular monosodium salt of carbapenem, at suitable reaction conditions. The stable carbon dioxide adduct of the carbapenem antibiotic formulation is useful for the treatment of bacterial infections in mammal patients, which can be administered intravenously or intramuscularly.

The present invention is directed to a process for preparing a final formulation product of a compound of Formula I,

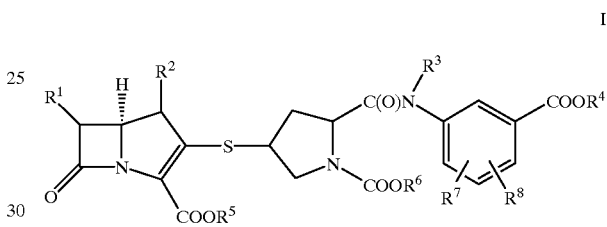

or its pharmaceutically acceptable salt, hydrate or solvate wherein, $R^1$ is:
(a) 1-hydroxyethyl,
(b) 1-fluoroethyl, or
(c) hydroxymethyl;

$R^2$ and $R^3$ are independently:
(a) hydrogen, or
(b) $(C_1-C_6)$-alkyl;

$R^4$, $R^5$, and $R^6$ are independently
(a) hydrogen
(b) $(C_1-C_6)$-alkyl, or
(c) alkali-metal or alkali earth-metal wherein the alkali-metal or alkali earth-metal is sodium, potassium, lithium, cesium, rubidium, barium, calcium or magnesium; and $R^7$ and $R^8$ are independently:
(a) hydrogen,
(b) halo,
(c) cyano,
(d) $(C_1-C_6)$-alkyl,
(e) nitro,
(f) hydroxy,
(g) carboxy,
(h) $(C_1-C_6)$-alkoxy,
(i) $(C_1-C_6)$-alkoxycarbonyl,
(j) aminosulphonyl,
(k) $(C_1-C_6)$-alkylaminosulphonyl,
(l) di-$(C_1-C_6)$-alkylaminosulphonyl,
(m) carbamoyl,
(n) $(C_1-C_6)$-alkylcarbamoyl, (o) di-($C_1$–$C_6$)-alkylcarbamoyl,
(p) trifluoromethyl,
(q) sulphonic acid,
(r) amino,
(s) ($C_1$–$C_6$)-alkylamino,
(t) di-($C_1$–$C_6$)-alkylmino,
(u) ($C_1$–$C_6$)-alkanoylamino,
(v) ($C_1$–$C_6$)-alkanoyl(N-($C_1$–$C_6$)-alkyl)amino,
(w) ($C_1$–$C_6$)-alkanesulphonamido, or
(x) ($C_1$–$C_6$)-alkyl-S(O)$_n$ wherein n is 0–2;
comprising the steps of:
(1) charging a solution of carbon dioxide source having a pH range of about 6.0 to about 12.0 into a reaction vessel;
(2) adding an effective amount of a mole ratio of a base and an active ingredient into the reaction vessel containing the solution of carbon dioxide source to maintain pH at about 6.0 to about 9.0 and a temperature range of about −3° C. to about 15° C.;
(3) lyophilizing the solution of Step (2) to yield the final formulation product of a compound of formula I with less than about 10% of moisture content.

A preferred embodiment of the present invention is a process for preparing a formulation of a compound of Formula Ia,

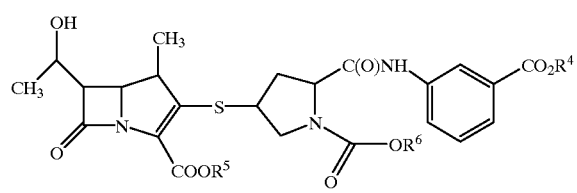

(Ia)

or its pharmaceutically acceptable salt, hydrates or solvate wherein,
$R^4$, $R^5$, and $R^6$ are independently:
(a) hydrogen
(b) ($C_1$–$C_6$)-alkyl, or
(c) alkali-metal or alkali earth-metal wherein the alkali-metal or alkali earth-metal is sodium, potassium, lithium, cesium, rubidium, barium, calcium or magnesium;
comprising the steps of:
(1) charging a solution of carbon dioxide source having a pH range of about 6.0 to about 12.0 into a reaction vessel;
(2) adding an effective amount of a mole ratio of a base and an active ingredient into the reaction vessel containing the solution of carbon dioxide source to maintain pH at about 6.0 to about 9.0 and a temperature range of about −3° C. to about 15° C.;
(3) lyophilizing the solution of Step (2) to yield the final formulation product of a compound of formula I with less than about 10% of moisture content.

An aspect of the process as recited above is where the carbon dioxide source is selected from the group consisting of carbon dioxide, sodium bicarbonate, potassium bicarbonate, sodium carbonate, potassium carbonate, calcium carbonate, cesium carbonate, magnesium carbonate, lithium carbonate, and a mixture thereof. The preferred carbon dioxide source is sodium bicarbonate.

Another aspect of the process recited above is where the carbon dioxide source in Step (1) is present in an amount relative to the amount of active ingredient, wherein a mole ratio of carbon dioxide source to the active ingredient is about 0.5 to about 1.5, preferably about 0.8 to about 1.2.

Yet another aspect of the process as recited above is where the pH range in Step (1) is about 7.0 to about 9.0.

Still another aspect of the process as recited above is where a temperature range in Step (1) is about −3° C. to about 15° C.

Still another aspect of the process as recited above is where the active ingredient is a compound of formula (a),

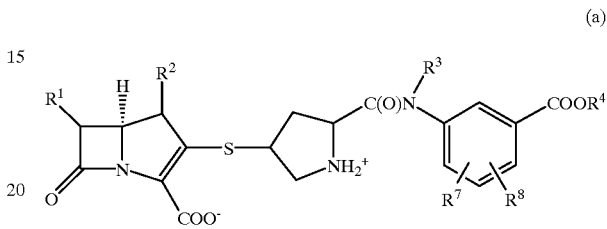

(a)

wherein $R^1$, $R^2$, $R^3$, $R^4$, $R^7$ and $R^8$ are as defined above.

Still another aspect of the process as recited above is where the preferred active ingredient is a compound of formula (a)'

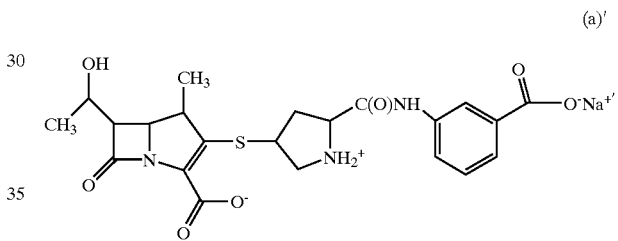

(a)'

Another aspect of the process as recited above is where the base is selected from the group consisting of sodium hydroxide, lithium hydroxide, potassium hydroxide, calcium hydroxide, barium hydroxide, magnesium hydroxide, lithium methoxide, sodium methoxide, potassium methoxide, calcium methoxide, lithium ethoxide, sodium ethoxide, potassium ethoxide, lithium tert-butoxide, sodium tert-butoxide and potassium tert-butoxide.

Yet another aspect of the process as recited above is where the base is sodium hydroxide at a concentration range of about 1N to about 3N.

Still another aspect of the process as recited above is where the effective amount of a mole ratio of a base to an active ingredient in Step (2) is about 0.7 to about 1.0.

Still another aspect of the process as recited above is where the mole ratio of a base to an active ingredient in Step (2) is about 0.8 to about 0.9.

Still another aspect of the process as recited above is where the pH range in Step (2) is about 7.0 to about 8.0.

Still another aspect of the process as recited above is where the temperature range in Step (2) is about −1° C. to about 5° C.

Still another aspect of the process as recited above is where the base is added followed by the addition of the active ingredient in Step (2).

Still another aspect of the process as recited above is where the temperature range in Step (2) is about −1° C. to about 5° C.

Still another aspect of the process as recited above is where the Step (2) further comprises a titration of the solution using a titrating agent to maintain the pH of the solution at a range of about 6.5 to about 8.5.

Still another aspect of the process as recited above is where the titrating agent is selected from the group consisting of sodium hydroxide, lithium hydroxide, potassium hydroxide, calcium hydroxide, barium hydroxide, magnesium hydroxide, lithium methoxide, sodium methoxide, potassium methoxide, calcium methoxide, lithium ethoxide, sodium ethoxide, potassium ethoxide, lithium tert-butoxide, sodium tert-butoxide and potassium tert-butoxide.

Still another aspect of the process as recited above is where the moisture content of the final formulation product is less than about 5%.

Still another aspect of the process as recited above is where the step (3) initially further comprises the following steps of:
(a) filtering the final formulation product into a receiving vessel using a sterilizing filter;
(b) aseptically filling the filtered final formulation product into a sterile vial; and
(c) placing a lyophilization stopper on the filled sterile vial containing the final formulation product.

It is further understood that the substituents recited above would include the definitions recited below, and unless otherwise stated or indicated, the definitions shall apply throughout the specification and claims.

As used herein, the term "alkyl" includes those alkyls of a designated number of carbon atoms of either a straight, branched or cyclic configuration. Examples of "alkyl" includes but are not limited to: methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, and the like.

The term "alkoxy" represents an alkyl group of indicated number of carbon atoms attached through an oxygen bridge, such as methoxy, ethoxy, propoxy, isopropoxy, butoxy, tert-butoxy, pentoxy, and the like.

The term "halogen" or "halo" refer to fluorine, chlorine, bromine and iodine.

As used herein, the term "1 mole equivalent" is defined as 1 mole of carbon dioxide source per 1 mole of active ingredient (or active drug), wherein carbon dioxide source includes carbon dioxide, sodium bicarbonate, potassium bicarbonate, sodium carbonate, potassium carbonate, calcium carbonate, cesium carbonate, magnesium carbonate, lithium carbonate, and a mixture thereof.

The term "active ingredient," also refers to as "bulk drug," "bulk active drug," "bulk active beta-lactam" or "bulk active carbapenem," refers to the amount of actual unstable, beta-lactam, carbapenem and/or alkali-metal salt or alkali earth-metal salt containing carbapenem removed from cold storage. The preferred active ingredient is a compound of formula of (a),

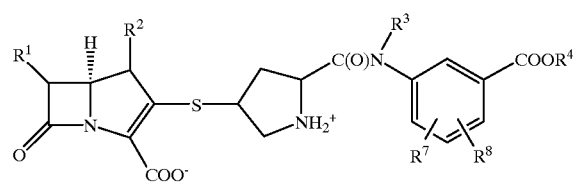

(a)

wherein
$R^1$ is:
(a) 1-hydroxyethyl,
(b) 1-fluoroethyl, or
(c) hydroxymethyl;

$R^2$ and $R^3$ are independently:
(a) hydrogen, or
(b) $(C_1-C_6)$-alkyl;
$R^4$, $R^5$, and $R^6$ are independently
(a) hydrogen
(b) $(C_1-C_6)$-alkyl, or
(c) alkali-metal or alkali earth-metal wherein the alkali-metal or alkali earth-metal is sodium, potassium, lithium, cesium, rubidium, barium, calcium or magnesium; and
$R^7$ and $R^8$ are independently:
(a) hydrogen,
(b) halo,
(c) cyano,
(d) $(C_1-C_6)$-alkyl,
(e) nitro,
(f) hydroxy,
(g) carboxy,
(h) $(C_1-C_6)$-alkoxy,
(i) $(C_1-C_6)$-alkoxycarbonyl,
(j) aminosulphonyl,
(k) $(C_1-C_6)$-alkylaminosulphonyl,
(l) di-$(C_1-C_6)$-alkylaminosulphonyl,
(m) carbamoyl,
(n) $(C_1-C_6)$-alkylcarbamoyl,
(o) di-$(C_1-C_6)$-alkylcarbamoyl,
(p) trifluoromethyl,
(q) sulphonic acid,
(r) amino,
(s) $(C_1-C_6)$-alkylamino,
(t) di-$(C_1-C_6)$-alkylmino,
(u) $(C_1-C_6)$-alkanoylamino,
(v) $(C_1-C_6)$-alkanoyl(N-$(C_1-C_6)$-alkyl)amino,
(w) $(C_1-C_6)$-alkanesulphonamido, or
(x) $(C_1-C_6)$-alkyl-S(O)$_n$ wherein n is 0–2;

The most preferred active ingredient is a compound of formula of (a)',

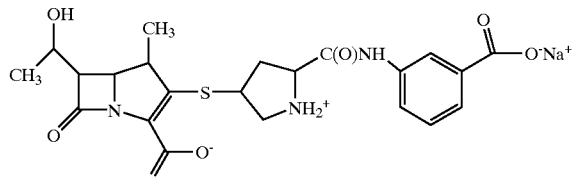

(a)'

The term "active drug," as used herein, is defined as the actual amount of beta-lactam, unstabilized and stabilized carbapenem, and alkali metal salt-containing carbapenem and carbon dioxide-containing carbapenem.

The term "quantum sufficit" ("q.s."), as used herein, is defined as the amount of a reagent necessary to increase the batch weight or volume to a specified total. As an example, a q.s. of 95% by wt % means the amount of reagent required to bring the weight percent up to 95% by weight based on 100% total weight.

The term "solid state stability" is defined as the ability of finished solid and lyophilized formulation (a porous off-white cake) at the end of about 2 years to deliver the prescribed and labeled dosage of active drug.

The term "reconstitution stability" is defined as the ability of a solution prepared by the finished solid and lyophilized formulation into an appropriate diluent (i.e. 0.9% saline for injection, 1% Lidocaine, and etc.) to deliver the prescribed and labeled dosage of active drug.

The batch-wise process of the present invention is carried out under aseptic conditions and requires several reagents and processing units to prepare formulations of high pharmaceutical quality. The present process provide a high rate conversion from the alkali metal salt, such as monosodium salt of carbapenem to the carbon dioxide adduct and the low by-product formation, such as dimers and open ring compounds. The reaction parameters and conditions such as the mole ratio of carbon dioxide source and active ingredient, mole ratio of base and active ingredient (active bulk carbapenem), reaction temperatures, pH of the solution, proper mixing, and appropriate lyophilization parameters are critical to obtain a final formulation product of high pharmaceutical quality.

The process for preparing a stable intravenous formulation of a carbon dioxide adduct of a carbapenem requires the processing temperature of about −3° C. to about 15° C., preferably about −1° C. to about 5° C., and the pH of the pre-lyophilized active solution to be about 6.0 to about 12.0, preferably about 7.0 to about 9.0. The process is carried out under aseptic conditions. All reagents used during the present processes meet *United States Pharmacopeia and National Formulary* standards unless otherwise stated.

Methods of preparing the compound of the present invention are illustrated in the following process and examples. They are provided for illustrative purposes and should not be construed as limiting the invention disclosed herein.

PROCESS

Sodium hydroxide solution of about 1N to about 3N is prepared by dissolving a sufficient amount of sodium hydroxide NF pellets in a sufficient amount of Water For Injection (WFI). While adding the sodium hydroxide, the solution is constantly mixed to ensure complete dissolution. The compounder/reactor (200L stainless steel jacketed vessel) is jacketed and cooled to maintain at a low temperature to prevent bulk drug degradation during the process. A variable agitation system is attached to the compounder/reactor to ensure complete dissolution of the bulk drug into solution. Generally, about 40% by weight or 60% by volume of WFI is charged into the compounder/reactor to begin the process, and the water is cooled to the temperature range of about −3° C. to about 15° C., preferably about −1° C. to about 5° C. To measure the pH of the solution in the compounder/reactor, appropriate pH and temperature devices are used. The pH meter is typically calibrated with buffer solution of pH 7.0 and 10.0. To maintain the pH of the solution within the required range during the batch-wise process, an appropriate pH controller system equipped with a pump is utilized to meter sodium hydroxide solution into the compounder/reactor.

After the WFI in the compounder/reactor is cooled, mixing is commenced to prevent localization of pH, temperature, and concentration of reagents and bulk antibiotic drug. A sufficient amount of carbon dioxide source such as sodium bicarbonate and/or sodium carbonate is added to the compounder/reactor under continuous mixing of the WFI to provide a final formulation concentration of about one mole equivalent (a mole ratio of carbon dioxide source to the active ingredient is about 0.5 to about 1.5, preferably about 0.8 to about 1.2). The solution is mixed until the carbon dioxide source, such as carbonates are completely dissolved. The pH of the solution is measured to ensure that it is about 6.0 to about 12.0, preferably about 7.0 to about 9.0 at a temperature range of about −3° C. to about 15° C. It is preferred that the temperature and pH of the solution be confirmed prior to beginning the addition of bulk drug. The unstable bulk carbapenem drug is removed from a refrigerated unit held at about −20° C. or lower and may be thawed to a temperature of from about 5° C. to about 25° C. for about 1 hour. A sufficient amount of the bulk drug is weighted out to provide a final formulation concentration of carbapenem to be about 200 g of active drug (as free acid)/liter formulation.

During the addition of the bulk active carbapenem to the compounder/reactor, the carbonate solution is constantly mixed. Generally, the mixing begins at lower agitation speed during the initial addition of bulk drug to the solution and as the amount of bulk in the solution is increased, mixing may be increased proportionally thereto. The primary purpose of mixing is to ensure complete dissolution of the bulk drug into the solution. As necessary, sodium hydroxide solution is added to the compounder/reactor during the addition of the bulk drug to maintain the pH of the solution to be about 6.0 to about 9.0, preferably about 7.0 to about 8.0. The bulk drug is generally slowly added to the compounder/reactor at a constant rate for about 30 minutes to about 90 minutes to enhance dissolution. At the end of the bulk drug addition, the solution is mixed for additional few minutes to ensure complete dissolution. The q.s. of the batch weight is adjusted to about 95% by weight of the final weight of the formulation with WFI, if needed, while maintaining the temperature at about −1° C. and about 5° C. Further titration using sodium hydroxide may be performed over a 10 minute to 20 minute period to ensure a mole ratio of base (NaOH) and bulk active drug to be in the range of from about 0.7 to about 1.0, preferably about 0.8 to about 0.9. Finally, the batch is adjusted to 100% by weight of its final weight with WFI with moderate mixing.

Afterwards, the solution is filtered through a sterilizing filter such as that from about 0.2 μm to about 0.25 μm. When making larger batches, generally from about 10L to about 200L in a compounder/rector, the compounding vessel is sealed and pressurized to initiate filtration. Filtration can be done either by pumping the solution through sterilizing filters with an appropriate pump in the absence of compounding vessel that can be pressurized or appropriate gas to carry out filtration by pressure. The receiving vessel should be sterile and cooled to a temperature range of about −3° C. to about 15° C. The density of the filtered formulation solution is generally about 1.0 g/mL to about 1.2 g/mL at about 0° C. to about 5° C., typically about 1.1 g/mL. Lyophilization of the completed formulation is preferred to simplified manufacture. However, the solution could be bulk lyophilized and the resulting powder filled into packages for use. If the processed by lyophilization in vials, the filtered formulation can be filled into vials and partially sealed with dry sterile siliconized lyophilization stoppers. In the following examples conventional 20 mL vials and 15 mL ADD-Vantage™ vials are utilized. The vials are filled at specified target fill and then placed onto lyophilizer shelves, which are pre-cooled to a temperature of about −40° C. to about −45° C., typically about −40° C. Suitable lyophilization cycle is then run with vials.

The lyophilization cycles used herein for the different vials are described in the examples below. Generally, the cycle requires the vials to be soaked at about −40° C. for about two hours and then heated to a temperature range of about −25° C. to about −15° C. shelf temperature at a rate of about 0.5° C./minute. The temperature is normally maintained at about −25° C. to about −15° C., and the pressure of the lyophilizer chamber is maintained at about 80 mTorr for about 48 hours to about 60 hours. The vials are heated to about 10° C. shelf temperature at a rate of about 0.1° C./minute and then to about 40° C. shelf temperature at a rate of about 0.5° C./minute, and maintained at 40° C. for up to about three hours at a pressure of about 80 mTorr or lower. The vials are then heated to about 60° C. shelf temperature at a rate of about 0.5° C./minute and held there at about 80 mTorr or less for about 3 hours to about 10 hours. The shelves are then cooled to ambient temperature (about 20° C.–30° C.). The vials are completely sealed under a partial vacuum of about 0.9 bar/700 Torr or lower before removing them from the lyophilizer. The vials are stored at a temperature not exceeding about 25° C. until needed.

EXAMPLE 1

At ambient temperature and pressure, a 2N sodium hydroxide solution was prepared by dissolving 20 g of sodium hydroxide NF pellets in 250 mL of water for injection (WFI) while mixing. A Beckman pH probe was calibrated using pH 7 and pH 10 buffers. Into a Kontes 317000–1000, one (1) liter glass, compounder/reactor vessel with jacketed cooler and agitator was charged 400 mL of WFI (about 50% of total batch volume), which was cooled to about 5° C. Thereafter, 28.0 g of sodium bicarbonate were dissolved into the compounder/reactor, and the compounder/reactor was held at a temperature of between about 1° C. and about 5° C., and a pH of between about 8.1 and about 8.5.

About 160 g of free acid, which is calculated from monosodium salt of carbapenem, exhibiting a moisture content of about 17.0% by weight were thawed to room temperature from −20° C. for about 30 minutes. The bulk drug was divided into ten equal portions and was gradually added to the sodium bicarbonate solution along with 2N NaOH solution for about 60 minutes to ensure complete dissolution. To reduce localization of pH, the 2N solution of sodium hydroxide was metered sub-surface into the compounder/reactor by a Masterflex peristaltic pump through size 16 tubing and a one foot long×1/16 inches diameter stainless steel dip tube. During the addition of the bulk drug and NaOH, the formulation solution was constantly agitated. The solution temperature was maintained between about 1° C. and about 6° C. and the pH at a set point of about 7.8 by adding sodium hydroxide solution. Following the addition of the bulk drug, the batch weight was adjusted to 95% of the final weight with WFI maintained at a temperature of about −1° C. to 5° C. to produce a bulk drug-sodium bicarbonate solution. While the bulk drug-sodium bicarbonate solution was agitated for an additional 20 minutes, 2N sodium hydroxide titration was performed that resulted in a mole ratio of sodium hydroxide to bulk drug of about 0.93. The final weight of the batch was adjusted to 100% total with chilled WFI at about −1° C. to about 5° C. with additional agitation for about 5 minutes. The total drug addition and compounding time was about 102 minutes, and the final batch weight was about 888.0 g.

While maintaining the solution at a temperature range of about −1° C. and about 5° C., the bulk drug-sodium bicarbonate solution was filtered utilizing a Sterivex GV filter unit containing a 0.22 µm filter into a sterile plastic container using a peristaltic pump. Immediately thereafter, about 6.33 g of the solution was placed into conventional 20 mL vials utilizing a manual filler, and the vials were frozen to about −70° C. The vials were partially stoppered and placed onto the shelves of a Virtis Lyophilizer pre-cooled to about −40° C. The lyophilizer was then operated according to the following cycle:

a) soak at about −40° C. shelf temperature for about two hours;

b) heat to about −20° C. shelf temperature at rate of about 0.5° C./min.;

c) hold shelf temperature at about −20° C. and about 80 mTorr pressure for about 48 hours;

d) heat to about 10° C. shelf temperature at rate of about 0.1° C./min;

e) heat to about 40° C. shelf temperature at rate of about 0.5° C./min.;

f) hold at about 40° C. and about 80 mTorr for about three hours;

g) heat to about 60° C. shelf temperature at rate of about 0.6° C./min.;

h) hold at about 60° C. and about 80 mTorr for about three hours;

i) cool the shelves to ambient temperature (about 20° C.–30° C.); and j) stopper under partial vacuum of about 0.9 bar/700 Torr.

Finally, the vials were removed from the lyophilizer as the final formulation. Table 1 provides the analysis results of the final formulation product.

TABLE 1

Analysis of the formulation product

| component | g/L | g/0.8 L |
|---|---|---|
| carbapenem | 200.0[a] | 160.0[a] |
| sodium bicarbonate | 35.0 | 28.0 |
| sodium hydroxide[b] | adjusted to pH 7.8 | adjusted to pH 7.8 |
| water for injection[c] | q.s 1.00 L | q.s. 0.8 L[d] |

[a]as free acid
[b]diluted in Water for Injection, and used as 2N solution for pH control
[c]removed during lyophilization
[d]q.s. 0.89 Kg based on 1.11 g/mL solution density The final product exhibited moisture content of about 1.91% w/w.

Table 2 illustrates the High Performance Liquid Chromatography (HPLC) results in area % of in process samples collected during the production of stabilized carbapenem antibiotic for this example.

TABLE 2

HPLC analysis of in-process samples

| | Carbapenem | Total Degradates | Total Dimers | Ring Open |
|---|---|---|---|---|
| | | HPLC, Area % | | |
| bulk drug | 98.6 | 1.4 | 0.5 | 0.7 |
| prefilter solution. | 97.6 | 2.3 | 1.1 | 1.0 |
| end of vial filling | 96.8 | 3.0 | 1.5 | 1.4 |
| lyophilized product | 95.6 | 4.4 | 1.6 | 2.5 |

EXAMPLE 2

The general procedure described in Example 1 was utilized to prepare the formulation of this example. Except for the parameter values provided in Table 3, identical conditions were applied in both examples. The final product exhibited moisture content of about 1.9% w/w. Table 4 illustrates the HPLC results in area % of in-process samples collected during the production of stabilized carbapenem antibiotic for this example.

TABLE 3

Compounding conditions

| | |
|---|---|
| drug addition time (min.) | 30 |
| total compounding time (min.) | 68 |
| pH set point during compounding | 7.4 |
| mole ratio of NaOH/Drug | 0.83 |

TABLE 4

HPLC analysis of in-process samples

| | Carbapenem | Total Degradates | Total Dimers | Ring Open |
|---|---|---|---|---|
| | HPLC, Area % | | | |
| carbapenem | 98.5 | 1.5 | 0.7 | 0.7 |
| prefilter solution | 98 | 1.9 | 0.9 | 0.9 |
| end of fill | 97.3 | 2.5 | 1.2 | 1.2 |
| lyophilized product | 95.9 | 4.1 | 1.5 | 2.3 |

EXAMPLES 3 AND 4

Examples 3 and 4 were carried out according to the same basic procedures described below with the exception of the parameters given in Table 5. The vials utilized in Example 3 were conventional 20 mL vials, whereas those utilized in Example 4 were ADD-Vantage™ 15 mL vials.

TABLE 5

Reaction conditions

| Image | Example 3 | Example 4 |
|---|---|---|
| drug addition time (min.) | 45 | 66 |
| total compounding time (min.) | 114 | 134 |
| pH controller set point during drug addition | 7.6 | 7.6 |
| pH controller set point during pH adjustment | 7.7 | 7.7 |
| mole ratio of NaOH added to active drug | 0.85 | 0.87 |
| filtration time (min.) | 30 | 31 |
| vial filling time (min.) | 203 | 157 |
| lyophilizer cycle time (min.) | 65 | 78 |

To prepare a pilot plant batch of the formulation, a 2N solution of sodium hydroxide was prepared by dissolving about 250 g of sodium hydroxide NF pellets in about 2000 g of WFI. While mixing, the solution was cooled to ambient temperature, and WFI was added to produce the final solution of about 3406 g. The sodium hydroxide solution was then chilled by using an Isotemp 1028S Chiller to a temperature of about 4° C. Into a 20L-stainless steel jacketed compounder/reactor, about 6.42 kg of the WFI was charged, and the solution was cooled to a target temperature of about −20° C. to about 5° C. The pH probe attached to a HD-PH-P pH Controller was standardized using pH 7.0 and pH 10.0 buffer solutions.

About 448 g of sodium bicarbonate was completely dissolved in the compounder/reactor, and the pH of the solution was measured at about 8.3. About 2560 g of unstabilized bulk drug (as free acid) was thawed from −20° C. to ambient temperature for approximately one hour and then divided into 10 equal portions. The 10 portions of bulk drug were added to the compounder/reactor for about 60 minutes while adding the sodium hydroxide solution via the pH controller to maintain the pH of bulk drug solution at about 7.6. At the end of the bulk drug addition, the solution was mixed for additional 15 minutes, and 2N NaOH titration was preformed to confirm complete dissolution of the bulk drug. After mixing again for another 15 minutes, water for injection at a temperature of about 0° C. to about 8° C. was added to bring the solution to about 97% of the total weight based on 100 total weight percent. While still mixing the solution, the pH was adjusted to about 7.7 with 2N NaOH solution to ensure that the mole ration of base (NaOH) to the bulk drug is within the range of about 0.8 to about 0.9. The weight of the solution was adjusted to 100 weight percent of the final batch weight by adding WFI at about 0° C. to about 8° C. while mixing for another five minutes. The compounder/reactor was then sealed and pressurized to about 15 psig to initiate filtration. The solution was then filtered through a Millipak 0.22 μm sterilizing filter into a sterile receiving vessel, which is continuously cooled to a temperature of about −1° C. to about 5° C. The filtered formulation solution exhibited a density of about 1.11 g/mL at about 5° C.

The sterile formulation was placed into sterile glass vials (6.33 g into 20 mL conventional vials, and 5.77 g into 15 mL ADD-Vantage™). The filled vials were partially stoppered with dry sterile siliconized lyophilization stoppers and placed onto lyophilizer shelves, which are pre-cooled to a temperature of about −45° C. to about −40° C. The lyophilizing procedure was conducted as follows:

20 mL Conventional Vials
  a) soak at about −40° C. (about −45° C. to −40° C.) lyo shelf temperature for at least two hours;
  b) heat to about −20° C. shelf temperature at about 0.5° C./minute;
  c) hold shelf temperature at about −20° C. and about 80 mTorr pressure for about 48 hours;
  d) heat to about 10° C. shelf temperature at about 0.1° C./minute;
  e) heat to about 40° C. shelf temperature at about 0.5° C./minute, and hold at about 40° C. and about 80 mTorr for about 3 hours;
  f) heat to about 60° C. shelf temperature at 0.5° C./minute, and hold at about 60° C. and about 80 mTorr for about 3 hours;
  g) cool the shelves to ambient temperature (about 20° C.–30° C.) before unloading; and
  h) stopper under partial vacuum (target of about 0.9 bar/700 Torr).

ADD-Vantage™ Vials
  a) soak at about −40° C. (about −45° to −40° C.) lyophilizer shelf temperature for at least 2 hours;
  b) heat to about −20° C. shelf temperature at about 0.5° C./minute;
  c) hold shelf temperature at about −20° C. and about 80 mTorr pressure for about 54 hours;
  d) heat to about −10° C. shelf temperature at about 0.1° C./minute, and hold at about −10° C. and about 80 mTorr for about 4 hours;

e) heat to about 10° C. shelf temperature at about 0.1° C./minute;

f) heat to about 40° C. shelf temperature at about 0.5° C./minute, and hold at about 40° C. and about 80 mTorr for about 3 hours;

g) heat to about 60° C. shelf temperature at about 0.5° C./minute, and hold at about 60° C. and about 80 mTorr for about 3 hours;

h) cool the shelves to ambient temperature (about 20° C.–30° C.) before unloading; and i) stopper under partial vacuum (target of about 0.9 bar/700 Torr).

After completion of the lyophilizing step, the vials containing the formulation were removed from the lyophilizer and capped (flip-off caps for conventional vials and ADD-Vantage caps for ADD-Vantage vials). The vials were then stored at a temperature of about 25° C. or below. Table 6 provide the analysis results of the final stabilized carbapenem antibiotic formulation.

TABLE 6

Analysis results of stabilized carbapenem antibiotic

| Component | g/L | g/12.8 L |
|---|---|---|
| carbapenem | 200.0 | 2560 |
| sodium bicarbonate | 35.0 | 448 |
| sodium hydroxide | adjusted to pH 7.5 | adjusted to pH 7.5 |
| WFI | q.s. 1.00 L | q.s. 12.8 L |

Table 7 summarizes the HPLC results of area % of in-processing samples collected during production of the batch of Example 3.

TABLE 7

HPLC analysis of in-process samples

| | Carbapenem | Total Degradates | Total Dimers | Ring Opening |
|---|---|---|---|---|
| | HPLC, Area % | | | |
| bulk carbapenem | 99.2 | 0.7 | 0.4 | 0.3 |
| pre-filtered solution | 97.6 | 2.2 | 1.0 | 1.2 |
| beginning of vial filling | 96.9 | 3.0 | 1.6 | 1.4 |
| middle of vial filling | 96.3 | 3.0 | 1.6 | 1.4 |
| end of vial filling | 95.7 | 4.3 | 2.5 | 1.7 |
| beginning of lyophilization | 95.5 | 4.4 | 1.7 | 2.5 |
| middle of lyophilization | 95.2 | 4.6 | 1.9 | 2.5 |
| end of lyophilization | 94.7 | 5.2 | 2.3 | 2.7 |

The final product moisture, as determined by NIR for Examples 3 and 4 were about 1.8% and about 2.1%, respectively.

What is claimed is:

1. A process for preparing a final formulation product of a compound of formula I,

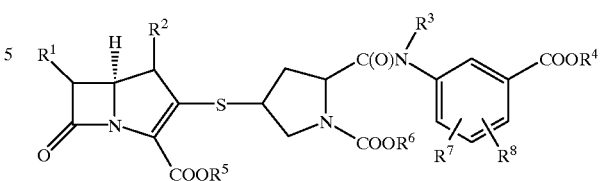

or its pharmaceutically acceptable salt, or hydrate wherein, $R^1$ is:
(a) 1-hydroxyethyl,
(b) 1-fluoroethyl, or
(c) hydroxymethyl;

$R^2$ and $R^3$ are independently:
(a) hydrogen, or
(b) $(C_1-C_6)$-alkyl;

$R^4$, $R^5$, and $R^6$ are independently
(a) hydrogen
(b) $(C_1-C_6)$-alkyl, or
(c) alkali-metal or alkali earth-metal wherein the alkali-metal or alkali earth-metal is sodium, potassium, lithium, cesium, rubidium, barium, calcium or magnesium; and $R^7$ and $R^8$ are independently:
(a) hydrogen,
(b) halo,
(c) cyano,
(d) $(C_1-C_6)$-alkyl,
(e) nitro,
(f) hydroxy,
(g) carboxy,
(h) $(C_1-C_6)$-alkoxy,
(i) $(C_1-C_6)$-alkoxycarbonyl,
(j) aminosulphonyl,
(k) $(C_1-C_6)$-alkylaminosulphonyl,
(l) di-$(C_1-C_6)$-alkylaminosulphonyl,
(m) carbamoyl,
(n) $(C_1-C_6)$-alkylcarbamoyl,
(o) di-$(C_1-C_6)$-alkylcarbamoyl,
(p) trifluoromethyl,
(q) sulphonic acid,
(r) amino,
(s) $(C_1-C_6)$-alkylamino,
(t) di-$(C_1-C_6)$-alkylmino,
(u) $(C_1-C_6)$-alkanoylamino,
(v) $(C_1-C_6)$-alkanoyl(N-$(C_1-C_6)$-alkyl)amino,
(w) $(C_1-C_6)$-alkanesulphonamido, or
(x) $(C_1-C_6)$-alkyl-$S(O)_n$ wherein n is 0–2;

comprising the steps of:
(1) charging a solution of carbon dioxide source having a pH range of about 6.0 to about 12.0 into a reaction vessel;
(2) adding an effective amount of a mole ratio of a base and an active ingredient into the reaction vessel containing the solution of carbon dioxide source to maintain pH at about 6.0 to about 9.0 and a temperature range of about −3° C. to about 15° C.;
(3) lyophilizing the solution of Step (2) to yield the final formulation product of a compound of formula I with less than about 10% of moisture content.

2. The process of claim 1, wherein the carbon dioxide source is selected from the group consisting of carbon dioxide, sodium bicarbonate, potassium bicarbonate, sodium carbonate, potassium carbonate, calcium carbonate, cesium carbonate, magnesium carbonate, lithium carbonate, and a mixture thereof.

3. The process of claim 2, wherein the carbon dioxide source is sodium bicarbonate.

4. The process of claim 3, wherein the carbon dioxide source in Step (1) is present in an amount relative to the amount of active ingredient, wherein a mole ratio of carbon dioxide source to the active ingredient is about 0.5 to about 1.5.

5. The process of claim 4, wherein the carbon dioxide source in Step (1) is present in an amount relative to the amount of active ingredient, wherein a mole ratio of carbon dioxide source to the active ingredient is about 0.8 to about 1.2.

6. The process of claim 5, wherein the pH range in Step (1) is about 7.0 to about 9.0.

7. The process of claim 6, wherein a temperature range in Step (1) is about −3° C. to about 15° C.

8. The process of claim 7, where the active ingredient is a compound of formula (a),

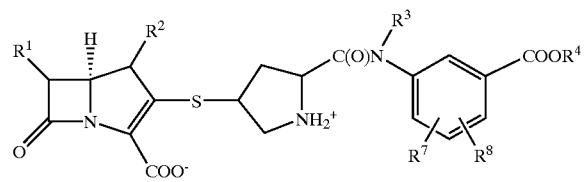

(a)

wherein $R^1$, $R^2$, $R^3$, $R^4$, $R^7$ and $R^8$ are as defined above.

9. The process of claim 8, wherein the base is selected from the group consisting of sodium hydroxide, lithium hydroxide, potassium hydroxide, calcium hydroxide, barium hydroxide, magnesium hydroxide, lithium methoxide, sodium methoxide, potassium methoxide, calcium methoxide, lithium ethoxide, sodium ethoxide, potassium ethoxide, lithium tert-butoxide, sodium tert-butoxide and potassium tert-butoxide.

10. The process of claim 9, wherein the base is sodium hydroxide at a concentration range of about 1N to about 3N.

11. The process of claim 10, wherein the effective amount of a mole ratio of a base to an active ingredient in Step (2) is about 0.7 to about 1.0.

12. The process of claim 11, wherein the mole ratio of a base to an active ingredient in Step (2) is about 0.8 to about 0.9.

13. The process of claim 12, wherein the pH range in Step (2) is about 7.0 to about 8.0.

14. The process of claim 13, wherein the temperature range in Step (2) is about −1° C. to about 5° C.

15. The process of claim 14, wherein the base is added followed by the addition of the active ingredient in Step (2).

16. The process of claim 15, wherein the temperature range in Step (2) is about −1° C. to about 5° C.

17. The process of claim 16, wherein the Step (2) further comprises a titration of the solution using a titrating agent to maintain the pH of the solution at a range of about 6.5 to about 8.5.

18. The process of claim 17, wherein the titrating agent is selected from the group consisting of sodium hydroxide, lithium hydroxide, potassium hydroxide, calcium hydroxide, barium hydroxide, magnesium hydroxide, lithium methoxide, sodium methoxide, potassium methoxide, calcium methoxide, lithium ethoxide, sodium ethoxide, potassium ethoxide, lithium tert-butoxide, sodium tert-butoxide and potassium tert-butoxide.

19. The process of claim 18, wherein the moisture content of the final formulation product is less than about 5%.

20. The process of claim 1, wherein the step (3) initially further comprises the following steps of:
 (a) filtering solution of Step 2 into a receiving vessel using a sterilizing filter;
 (b) aseptically filling the filtered solution of Step 2 into a sterile vial; and
 (c) placing a lyophilization stopper on the filled sterile vial containing the solution of step 2.

21. A process for preparing a final formulation product of a compound of Formula Ia,

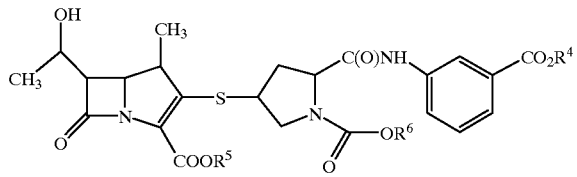

Ia or its pharmaceutically acceptable salt, or hydrates wherein, $R^4$, $R^5$, and $R^6$ are independently:
 (a) hydrogen
 (b) ($C_1$–$C_6$)-alkyl, or
 (c) alkali-metal or alkali earth-metal wherein the alkali-metal or alkali earth-metal is sodium, potassium, lithium, cesium, rubidium, barium, calcium or magnesium;
comprising the steps of:
 (1) charging a solution of carbon dioxide source having a pH range of about 6.0 to about 12.0 into a reaction vessel;
 (2) adding an effective amount of a mole ratio of a base and an active ingredient into the reaction vessel containing the solution of carbon dioxide source to maintain pH at about 6.0 to about 9.0 and a temperature range of about −3° C. to about 15° C.;
 (3) lyophilizing the solution of Step (2) to yield the final formulation product of a compound of formula Ia with less than about 10% of moisture content.

22. The process of claim 21, wherein the carbon dioxide source is selected from the group consisting of carbon dioxide, sodium bicarbonate, potassium bicarbonate, sodium carbonate, potassium carbonate, calcium carbonate, cesium carbonate, magnesium carbonate, lithium carbonate, and a mixture thereof.

23. The process of claim 22, wherein the carbon dioxide source is sodium bicarbonate.

24. The process of claim 23, wherein the carbon dioxide source in Step (1) is present in an amount relative to the amount of active ingredient, wherein a mole ratio of carbon dioxide source to the active ingredient is about 0.5 to about 1.5.

25. The process of claim 24, wherein the carbon dioxide source in Step (1) is present in an amount relative to the amount of active ingredient, wherein a mole ratio of carbon dioxide source to the active ingredient is about 0.8 to about 1.2.

26. The process of claim 25, wherein the pH range in Step (1) is about 7.0 to about 9.0.

27. The process of claim 26, wherein a temperature range in Step (1) is about −3° C. to about 15° C.

28. The process of claim 27, where the active ingredient is a compound of formula (a)',

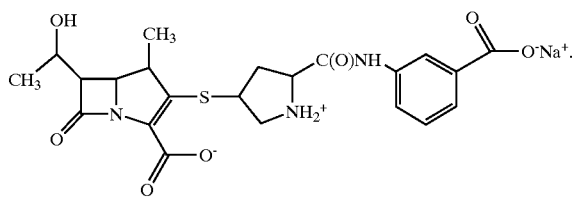

(a)'

29. The process of claim 28, wherein the base is selected from the group consisting of sodium hydroxide, lithium hydroxide, potassium hydroxide, calcium hydroxide, barium hydroxide, magnesium hydroxide, lithium methoxide, sodium methoxide, potassium methoxide, calcium methoxide, lithium ethoxide, sodium ethoxide, potassium ethoxide, lithium tert-butoxide, sodium tert-butoxide and potassium tert- butoxide.

30. The process of claim 29, wherein the base is sodium hydroxide at a concentration range of about 1N to about 3N.

31. The process of claim 30, wherein the effective amount of a mole ratio of a base to an active ingredient in Step (2) is about 0.7 to about 1.0.

32. The process of claim 31, wherein the mole ratio of a base to an active ingredient in Step (2) is about 0.8 to about 0.9.

33. The process of claim 32, wherein the pH range in Step (2) is about 7.0 to about 8.0.

34. The process of claim 33, wherein the temperature range in Step (2) is about −1° C. to about 5° C.

35. The process of claim 34, wherein the base is added followed by the addition of the active ingredient in Step (2).

36. The process of claim 35, wherein the temperature range in Step (2) is about −1° C. to about 5° C.

37. The process of claim 36, wherein the Step (2) further comprises a titration of the solution using a titrating agent to maintain the pH of the solution at a range of about 6.5 to about 8.5.

38. The process of claim 37, wherein the titrating agent is selected from the group consisting of sodium hydroxide, lithium hydroxide, potassium hydroxide, calcium hydroxide, barium hydroxide, magnesium hydroxide, lithium methoxide, sodium methoxide, potassium methoxide, calcium methoxide, lithium ethoxide, sodium ethoxide, potassium ethoxide, lithium tert-butoxide, sodium tert-butoxide and potassium tert- butoxide.

39. The process of claim 38, wherein the moisture content of the final formulation product is less than about 5%.

40. The process of claim 21, wherein the step (3) initially further comprises the following steps of:
    (a) filtering the solution of Step 2 into a receiving vessel using a sterilizing filter;
    (b) aseptically filling the filtered solution of step 2 into a sterile vial; and
    (c) placing a lyophilization stopper on the filled sterile vial containing the solution of Step 2.

* * * * *